(12) United States Patent
Luck

(10) Patent No.: US 6,835,864 B2
(45) Date of Patent: Dec. 28, 2004

(54) METHOD AND DEVICE FOR TREATING MINOR WOUNDS

(76) Inventor: Aaron John Luck, 1806 Parkview Dr. South, Montgomery, AL (US) 36117

( * ) Notice: Subject to any disclaimer, the term of this patent is extended or adjusted under 35 U.S.C. 154(b) by 586 days.

(21) Appl. No.: 09/947,636

(22) Filed: Sep. 5, 2001

(65) Prior Publication Data

US 2003/0045864 A1 Mar. 6, 2003

(51) Int. Cl.$^7$ ............................ A61F 13/00; A61L 15/00
(52) U.S. Cl. ............................................ 602/56; 206/440
(58) Field of Search ............................. 206/440, 441, 206/363, 828; 600/583; 602/41–59

(56) References Cited

U.S. PATENT DOCUMENTS

| | | |
|---|---|---|
| 3,113,560 A | 12/1963 | Robins |
| 3,328,259 A | 6/1967 | Anderson |
| 4,022,203 A | 5/1977 | Ackley |
| 4,233,976 A | 11/1980 | Dunshee et al. |
| 5,830,170 A | 11/1998 | Whiteman et al. |

*Primary Examiner*—Weilun Lo
*Assistant Examiner*—Linh Truong
(74) *Attorney, Agent, or Firm*—Bradley Arant Rose & White LLP

(57) ABSTRACT

Disclosed is a device and material which assist in the coagulation and containment of blood from a wound produced as a result of medical procedures which require blood to be drawn, such as with a lancet or a needle or the like. The device is a compact, portable unit that dispenses an appropriate amount of absorbent material for the collection and coagulation of blood. The absorbent material comprises a non-absorbent backing coupled with an absorbent top layer. The absorbent material may also contain medicaments that assist in the coagulation and wound healing process.

17 Claims, 4 Drawing Sheets

METHOD AND DEVICE FOR TREATING MINOR WOUNDS

FIELD OF THE INVENTION

The disclosure relates to devices and materials for assisting in the coagulation and containment of blood. More specifically, the disclosure relates to devices and materials for assisting in the coagulation and containment of blood from a wound produced as a result of medical procedures which require blood to be drawn.

BACKGROUND OF THE INVENTION

Diabetes has become a serious medical condition in the United States and worldwide. Estimates are that more than 16 million individuals in the United States suffer from diabetes and more than 120 million individuals worldwide. The World Health Organization estimates that by the year 2025 diabetes will affect more than 300 million people worldwide.

Diabetics are divided into two groups-insulin dependant and non-insulin dependent. As the name suggests, the insulin dependent diabetics require daily injections of insulin. Similarly, non-insulin dependent diabetics usually rely upon oral medications, diet and exercise, but in some cases also utilize injectable insulin.

Regardless of the classification, all diabetics require regular blood testing which monitors their glucose levels and ensures that they are maintaining as close-to-normal glucose levels as possible. This glucose testing requires a blood sample which is most commonly taken from the finger, and most recently can be taken from the arm. The most common method of performing this test is to use a lancet or similar device which pushes a small needle into the finger or arm. This, in turn, causes a minor wound to the finger or arm which causes blood to be released. This blood is then drawn and transferred to a machine which is specially designed to measure the amount of glucose present in the blood. This process is usually performed several times a day to ensure that blood glucose levels are acceptable. This testing allows the diabetic to adjust diet, exercise or medication to achieve optimal blood-glucose levels.

As described above the blood monitoring tests result in a small lancet or needle wound, usually in the finger or arm. Although the wound is minor in nature, the wound is inflicted several time a day, every day, in most cases for the life of the patient. Since the wound is minor in nature, it requires only a small amount of material to stop the bleeding. However, application of some material to the wound to aid in the clotting process is essential, as the wound will continue to bleed for a considerable time without such material.

Although there are countless products currently available to assist diabetics in almost all aspects of their care, there are no products specifically designed for the simple and efficient treatment of wounds inflicted as a result of the blood testing process. Although several alternatives are available to diabetics, they all suffer from one or more disadvantages. Standard bandages or dressings or are too bulky for convenient placement on the finger or arm. Furthermore, since the wound caused by a lancet or needle will usually stop bleeding within several minutes, bandages or dressings are too permanent in nature. Finally, bandages and dressings provide a great excess of material over that which is required to initiate the coagulation process at the wound site. Sterile adhesive strips, or band-aids, are also often too bulky for convenient use and provide more material than is needed to stop the bleeding associated with the wound. In addition, removal of the adhesive strip may cause some discomfort to users, especially when repeated several times a day. Finally, the adhesives in the sterile strips or the adhesives that secure some types of bandages and dressings have been known to cause allergic reactions in some individuals, with the reactions becoming more common the longer the individual is exposed to the adhesive. Therefore, bandages, dressing and adhesive strips are unnecessary, inconvenient and result in a substantial amount of waste.

Since the products currently on the market are not satisfactory solutions for the treatment of wounds caused by the blood testing process, diabetics and others who must routinely test their blood are forced to rely on items designed for other uses, such as paper towels, napkins, tissue paper or similar items. Since these items are too large for use on such small areas, individuals are required to tear-off pieces of the product for use. Again, this results in wasted material, substantial inconvenience and the necessity for the individual to carry bulky products around with them.

A similar problem exists in healthcare offices, laboratories and doctors' offices and other locations where blood is routinely drawn. The instant disclosure would be equally applicable in these situations as well.

Therefore, what is needed is a compact, portable device for dispensing an appropriate amount of absorbent material for the containment and coagulation of blood associated with minor wounds, such as those caused by blood testing procedures. Such a device would be practical for all individuals that were required to monitor or test their blood on a regular basis. In addition, the device would also be useful in the medical office or clinical situation.

BRIEF DESCRIPTION OF THE DRAWINGS

These and other objects of the present disclosure, as well as its advantages and capabilities, will be more fully understood by reference to the following detailed description when considered in connection with the accompanying drawings in which.

DETAILED DESCRIPTION

The device of the present disclosure is a compact, refillable dispensing apparatus which aids in the coagulation and containment of blood from a wound produced as a result of blood being drawn. The device dispenses an appropriate amount of absorbent material for the collection and coagulation of blood from such a wound. The absorbent material comprises a non-absorbent backing coupled with an absorbent top layer, and may also contain medicaments that assist in the coagulation and wound healing process.

Figure 1A:
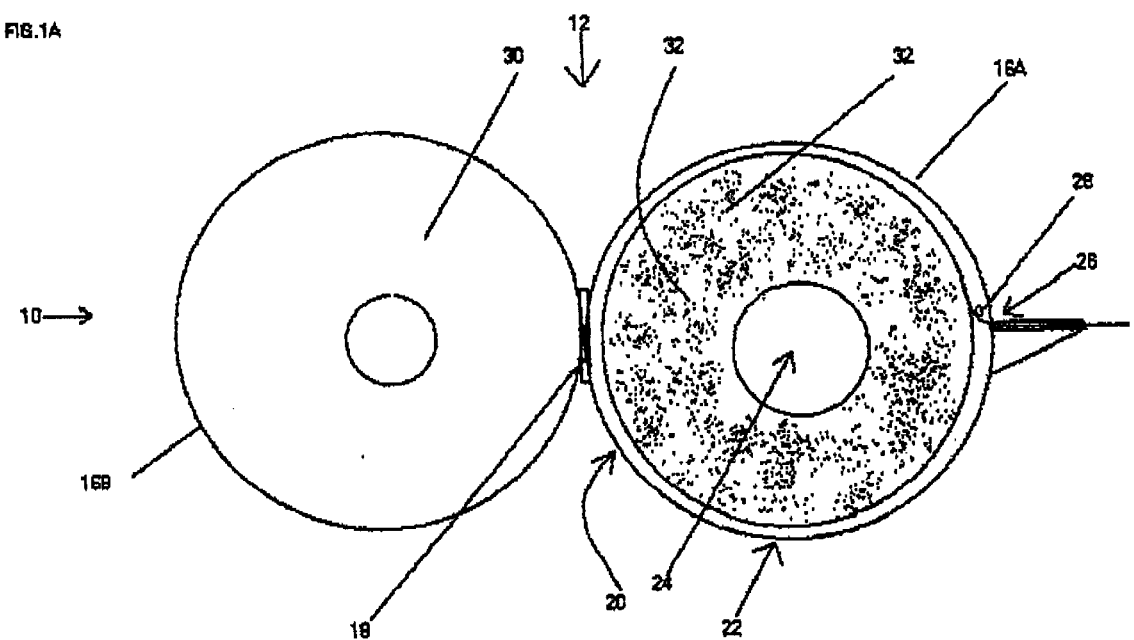
FIG. 1A is a frontal elevation view of one embodiment of the device, illustrating the device in an open configuration.
Figure 1B:
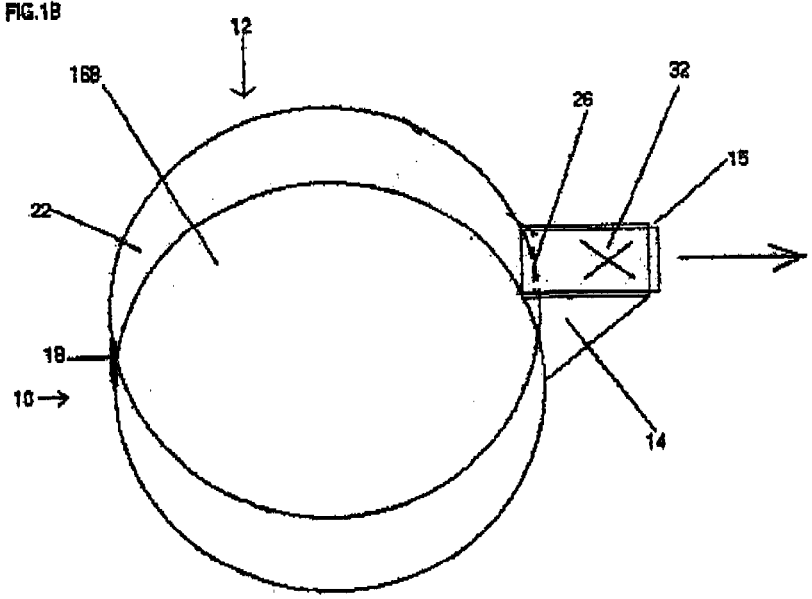
FIG. 1B is a frontal elevation view of one embodiment of the device, illustrating the device in a closed configuration.

One embodiment of the device 10 is illustrated in FIGS. 1A and 1B. As illustrated in FIG. 1A, the device 10 comprises a protective outer body 12, a finger receiving means and a tensioning means. Although the exact configuration of the outer body 12 is not critical, FIGS. 1A & 1B show outer body 12 in a circular or spherical configuration. In the embodiment shown in FIG. 1A, the outer body 12 further comprises a base 16A and a cover 16B joined together by a connecting means. Although the device 10 is shown comprising two pieces to facilitate replacement of the absorbent material, the outer body 12 may be composed of a single piece. In the latter case, the apparatus would be a single use, disposable device rather than multi-use, refillable device. In FIGS. 1A and 1B, the connecting means is illustrated as hinge 18, although other means could be used, such as a male/female threaded coupling, a pin, a pressure connection, luer coupling, snap-fit coupling or bayonet coupling. Base 16A preferably comprises a bottom 20, an outer wall 22 joined to bottom 20, a sprocket 24 joined to bottom 20, a slot 26 in the outer body 12 and a tension means to regulate the dispensing of the absorbent material 32. The base 20, outer wall 22 and sprocket 24 form a cavity 30 to receive the absorbent material 32. In FIG. 1A, the tensioning means is illustrated as tensioning spring 28. Alternative means to regulate the dispensing of the absorbent material include a set of rubber rollers, with one of the rollers positioned above the absorbent material and the other roller positioned below the absorbent material.

The finger receiving means serves to receive both the finger (shown in FIGS. 4A and 4B) and the absorbent material 32 and provides a stable surface against which the finger can be pressed against the absorbent material 32. The size and configuration of the finger receiving means is sufficient to receive the finger comfortably. In FIGS. 1A and 1B, the finger receiving means is illustrated as platform 14. Platform 14 has a cutting edge 15 on one of its sides, preferably the front side, and supports a section of absorbent material 32. Platform 14 is securely attached to outer wall 22. The platform 14 extends from the outer wall 22 a sufficient distance to receive an pre-determined amount of absorbent material. This distance may correspond to the distance between the perforations 54 in the absorbent material 32 (illustrated in FIG. 3A). In this manner, the cutting edge 15 is lined-up with the perforation 54 when a portion of the absorbent material 32 is pulled-out from the cavity 30. This will enable easy tearing at the perforation 54 since a downward motion will result in the platform providing resistance at the perforation 54 of the absorbent material 32.

In an alternate embodiment, the finger receiving means may be a platform or base housed in a cavity or indentation formed inside the outer body. As described above, the platform or base area receives the absorbent material and the finger. The platform or base may have a cutting edge on one side. The platform or base may be a separate element, or a flat portion of the outer body itself. In this embodiment, the tip of the finger is placed within the cavity or indentation on the platform or base.

Figure 2A:
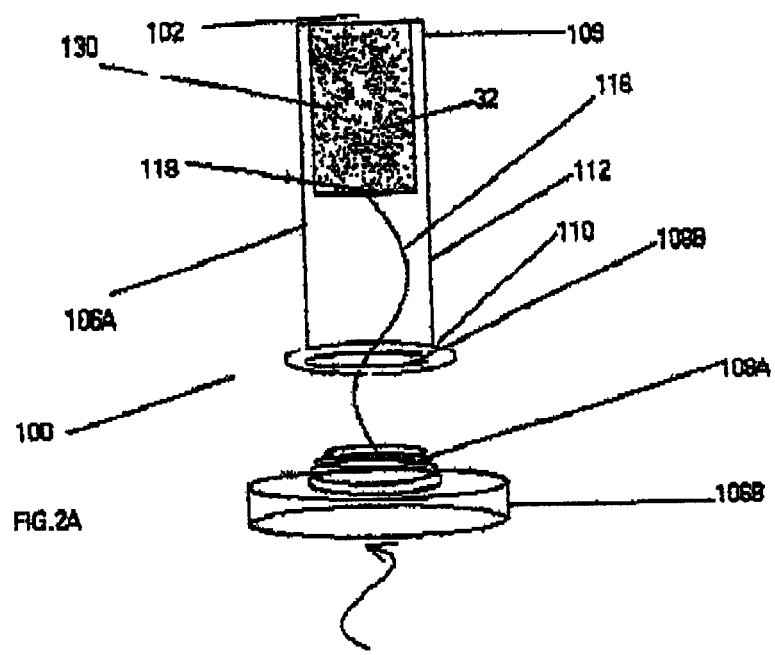
FIG. 2A is a partially exploded frontal elevation view of an alternate embodiment of the device.
Figure 2B:
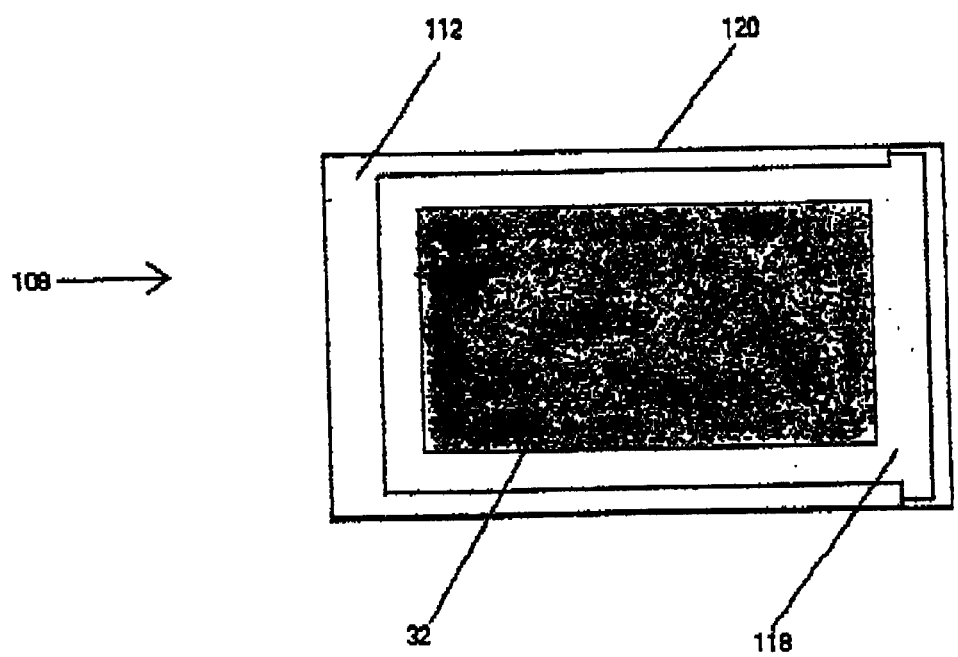
FIG. 2B is a top elevation view of the device illustrated in FIG. 2A.

An alternate embodiment of the device is shown in FIGS. 2A and 2B. The device 100 comprises an outer body 102, a finger receiving means and a tensioning means. Although the configuration of outer body 102 is not critical to the present invention, FIG. 2A shows body 102 in a rectangular configuration. The outer body 102 further comprises a cover 106A and a base 106B, joined together by a connecting means. In FIG. 2A, the connecting means is illustrated as a male and female threaded coupling 108A and 108B, respectively, although other means could be used, such as a hinge, a pin, a pressure connection, luer coupling, snap-fit coupling or bayonet coupling. Cover 106A has an upper end 109 and a lower end 110 joined by 4 walls 112. As illustrated in FIGS. 2A and 2B, the upper end 109 and the lower end 110 are at least partially open. The upper end 109, lower end 110 and walls 112 define a cavity 130 to receive the absorbent material 32. The lower end 110 of cover 106A comprises a female threaded coupling 108B. The base 106B comprises male threaded connection 108A and the means to advance the absorbent material. In FIG. 2A, the means is shown as a tensioning spring 116 secured at one end to the base 106B and secured at the other end to platform 118. The configuration of platform 118 is such that it fits into cavity 130. FIG. 2B illustrates the finger receiving means of device 100. In FIG. 2B the receiving means comprises the platform 118. At least one lip 120 extends at a substantially perpendicular angle from at least one of the walls 112 and serves to secure the absorbent material on platform 118.

The device can be manufactured from a variety of materials, including, but not limited to, plastic, metal or a composite material. It is preferred that the material be strong and lightweight, such as plastic. The overall configuration of the device should be as compact as possible for ease of use. As illustrated in FIGS. 1A and 2, the unit is constructed so it can be opened to receive additional absorbent material allowing the device to be re-used. Such a design would have the primary purpose of allowing the refillable material to be placed into the dispensing unit and closed securely. Alternatively, the device could be constructed so that it cannot be opened, allowing the device to be disposed of when the initial supply of absorbent material is exhausted. The device can also be manufactured is a variety of colors, designs or themes to accommodate and appeal to both adults and children alike. The embodiments discussed above are illustrative only and should not be considered to limit the present disclosure.

Figure 3A:
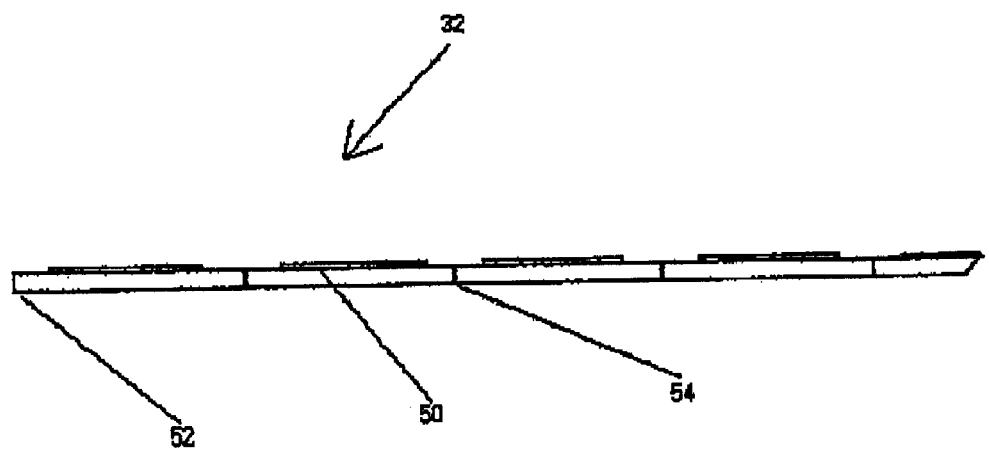
FIG. 3A is a frontal elevation view of one embodiment of the absorbent material.
Figure 3B:
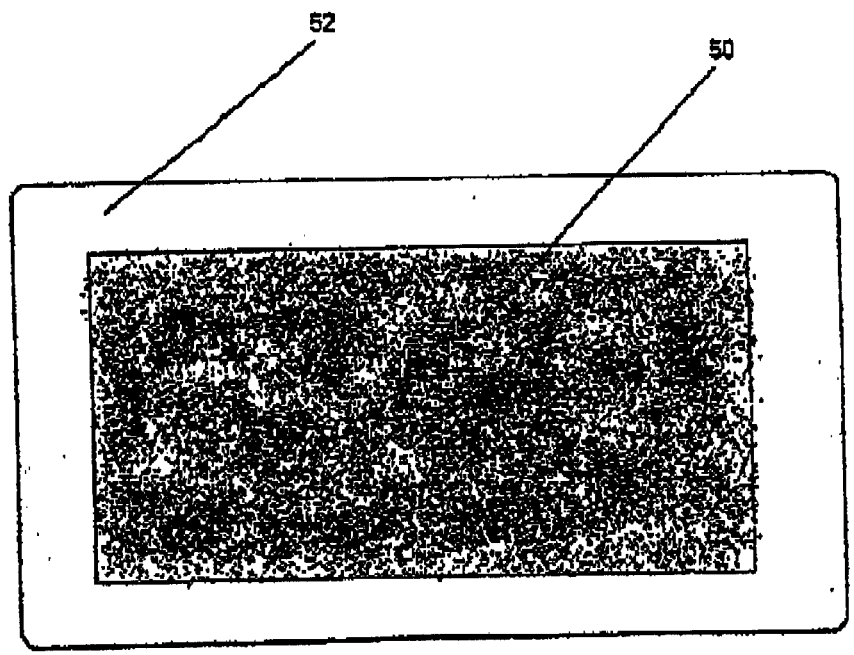
FIG. 3B is a frontal elevation view of an alternate embodiment of the absorbent material.
Figure 4A:
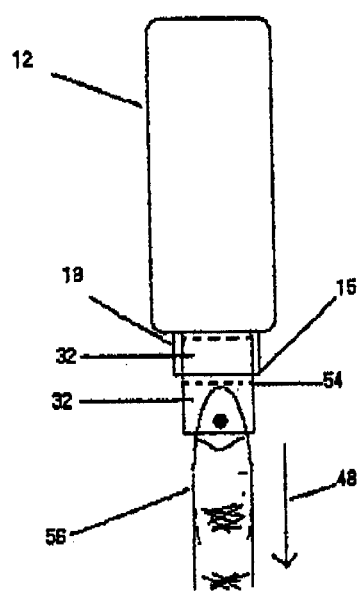
FIG. 4A is a top view of the device of FIG. 1A in use.

As illustrated in FIGS. 3A and 3B, the absorbent material 32 comprises an absorbent side 50 and a non-absorbent side 52 securely bonded together. The absorbent side 50 is constructed from a material which will absorb and contain blood, thereby assisting in the coagulation process. The exact nature of the absorbent side 50 is not critical so long as the above functions are accomplished, but suitable materials may include gauze, paper, tissue or similar materials. The non-absorbent side 52 is constructed from material that is impervious to liquid, such as plastic. The non-absorbent layer serves to provide containment of the blood and prevents blood from seeping through the absorbent material and contaminating or soiling other objects (for example, clothing). As shown in FIG. 3B, the non-absorbent side 52 may be somewhat larger than the absorbent side 50. Optionally, the absorbent side 50 may contain a quantity of medicament sufficient to aid in the coagulation process.

The absorbent material may be provided in any convenient form, and the exact form will be dictated in a large part by the nature of the device used to dispense the absorbent material. For example, the device illustrated in FIGS. 1A and 1B would require the absorbent material to be in the form of a roll. FIG. 3A illustrates an embodiment of the absorbent material in linear form which can be supplied as a roll. Note that perforations 54 are present at predetermined intervals to aid in removing individual sections of absorbent material after use. However, the device illustrated in FIG. 2A would require the absorbent material be individual sections in the shape of rectangle or square. The exact dimensions for the absorbent material may be adjusted if more or less absorbent material is required, or if the particular device used requires different dimensions.

In operation, the user will first "load" the device with the appropriate absorbent material if the device is a multi-use refillable unit. For the device shown in FIG. 1A, the user will place the absorbent material 32 on sprocket 24 in cavity 30 and thread the absorbent material 32 through slot 26 so that a portion of the absorbent material 32 rest on platform 14. Otherwise, the device will be supplied with the absorbent material 32 in the proper position for use. The absorbent material is held in place on platform 14 by tension spring 28 The user then places the finger 56 so that the wound contacts the absorbent material 32 and presses down against the platform 14. The pressure allows the absorbent material 32 to slow the flow of blood from the wound and aid in the coagulation process, thereby stopping the bleeding. After a sufficient amount of time, usually only seconds, the user removes the finger 56 from the platform 14 in the direction of arrow 50, which pulls the absorbent material 32 forward drawing additional absorbent material 32 onto platform 14 (see FIG. 4A). The used absorbent material is removed by pulling the absorbent material 32 downward against cutting edge 15 and/or by the presence of perforations 54. Once removed, the soiled absorbent material can be disposed of.

Figure 4B:
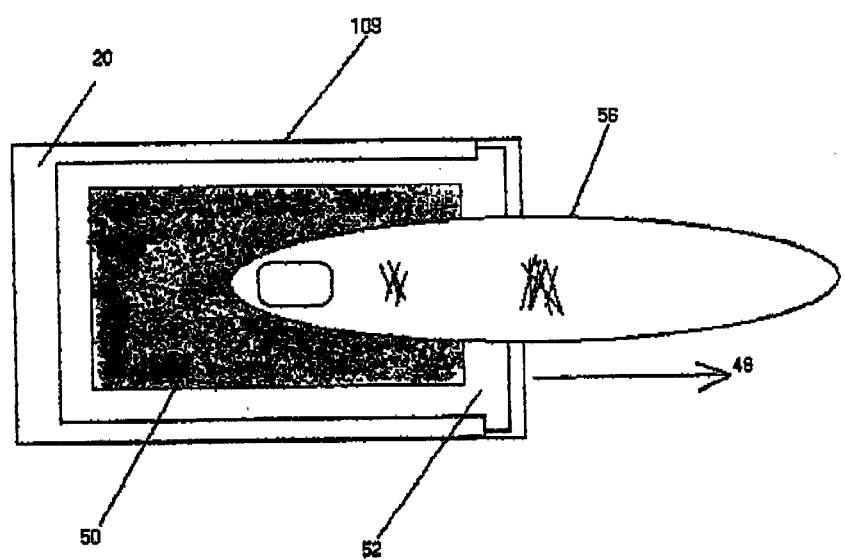
FIG. 4B is a top view of the device of FIG. 2A in use.

The alternate embodiment of the device shown in FIG. 2 operates in a similar manner. However, instead of the absorbent material being dispensed in a continuous roll, which requires the user to separate the individual sheets after use, the absorbent material is provided in separate sections. Referring to FIG. 3B, the individual squares of absorbent material are placed on the receiving platform 118. The cover 106A is secured to base 106B so that the absorbent material is within cavity 130. Placement of the cover 106A over the absorbent material creates tension in tension spring 116, which forces the individual squares of absorbent material against lip 120 at the upper end 109 of the cover 106A. This pressure holds the material securely in place until removed by the user. As shown in FIG. 4B, the user places the finger 56 with the wound on the absorbent material 32 and presses down. The pressure allows the absorbent material 32 to slow the flow of blood from the wound and aid in the coagulation process, thereby stopping the bleeding from the wound. After a sufficient amount of time, usually only seconds, the user removes the finger 56 in the direction of arrow 52. The absorbent material adheres slightly to the finger, removing that piece of absorbent material 32. A replacement section of absorbent material 32 is put in position and available for use as a result of the action of tension spring 116. It should be noted that after use of any embodiment of the device, there is no excess absorbent material or backing material associated with or trailing from the device that requires separate disposal as was the case with some prior art devices.

The device and absorbent material of the present disclosure allow a user to stop the flow of bleeding from a minor wound, such as that caused by blood testing procedures, quickly and efficiently. Because of the portable nature of the device, the daily routine of the user is not upset or altered. In addition, since the absorbent material is provided in sizes convenient for the small nature of the wound material is not wasted.

The above discussion has described several embodiments of the device in detail so that the device and its principles of operation may be understood. The above discussion should not be interpreted to exclude additional embodiments of the device. With respect to the above description, it should be considered that the optimal dimensional relationships for the various parts of the device, including variations in size, materials, shape, form, function and manner of operation, assembly and use, are readily apparent to one of ordinary skill in the art, and all equivalent relationships to those described above and illustrated in the figures are intended to be encompassed by the present disclosure. Therefore, the foregoing is considered illustrative only, and should not be understood to limit the scope of the disclosure to the exact construction and operation discussed and illustrated.

What is claimed is:

1. A device to aid in the containment and coagulation of blood from a wound, the device comprising
   a. an outer body, the outer body further comprising a base and a cover, the base and the cover joined together by a connecting means and forming a cavity adapted to receive an absorbent material;
   b. a finger receiving means in communication with the outer body to receive a finger and the absorbent material;
   c. a dispensable supply of absorbent material contained at least partially within the outer body; and
   d. a tensioning means on the outer body to regulate the dispensing of the absorbable material.

2. The device of claim 1 where the finger receiving means is a platform or base, the connecting means is selected from the group consisting of a threaded coupling, a hinge, a pin, a pressure connection, a luer coupling, a snap-fit coupling or a bayonet coupling and the tensioning means is selected from the group consisting of a tensioning spring and a set of rubber rollers.

3. The device of claim 1 where the absorbent material is provided as a roll of absorbent material, the roll of absorbent material being divided into sections by a plurality of perforations at pre-determined locations thereon.

4. The device of claim 1 where the absorbent material is provided as a plurality of individual sections, the individual sections stacked one atop the other.

5. The device of claim 1 where the outer body is substantially circular.

6. The device of claim 1 where the outer body is substantially rectangular.

7. The device of claim 1 where the outer body is substantially oval.

8. A device to aid in the containment and coagulation of blood from a wound, the device comprising
   a. an outer body, the outer body forming a cavity adapted to receive an absorbent material;
   b. a finger receiving means in contact with the outer body to receive a finger and the absorbent material;
   c. a dispensable supply of absorbent material contained at least partially within the outer body; and
   d. a tensioning means on the outer body to regulate the dispensing of the absorbable material.

9. The device of claim 8 where the finger receiving means is a platform or base and the tensioning means is selected from the group consisting of a tensioning spring and a set of rubber rollers.

10. The device of claim 8 where the absorbent material is provided as a roll of absorbent material, the roll of absorbent material being divided into sections by a plurality of perforations at pre-determined locations thereon.

11. The device of claim 8 where the absorbent material is provided as a plurality of individual sections, the individual sections stacked one atop the other.

12. The device of claim 8 where the outer body is substantially circular.

13. The device of claim 8 where the outer body is substantially rectangular.

14. The device of claim 8 where the outer body is substantially oval.

15. An absorbent material to aid in the containment and coagulation of blood from a wound comprising a first layer securely bonded to a second layer, the first layer being an absorbent layer and the second layer being impermeable to liquid.

16. The absorbent material of claim 15 further comprising perforations at predetermined locations thereon.

17. The absorbent material of claim 16 where the top layer contains a quantity of medicament sufficient to assist in the blood coagulation process.

* * * * *